(12) United States Patent
Aiolfi et al.

(10) Patent No.: US 7,399,266 B2
(45) Date of Patent: Jul. 15, 2008

(54) METHOD AND MACHINE FOR FOLDING AND FINISHING TRAINING PANT DIAPERS

(75) Inventors: Luca Aiolfi, Izano (IT); Matteo Piantoni, Albino (IT); Stefano Nanni, Bergamo (IT); Alberto Perego, Milan (IT)

(73) Assignee: GDM S.p.A., Bologna (IT)

( * ) Notice: Subject to any disclaimer, the term of this patent is extended or adjusted under 35 U.S.C. 154(b) by 12 days.

(21) Appl. No.: 11/439,246

(22) Filed: May 24, 2006

(65) Prior Publication Data

US 2006/0276320 A1    Dec. 7, 2006

(30) Foreign Application Priority Data

May 25, 2005   (IT)   ............ BO2005A0360

(51) Int. Cl.
*B31F 1/08*    (2006.01)
(52) U.S. Cl. .............. 493/424; 493/418; 493/450
(58) Field of Classification Search ........... 493/424, 493/418, 450, 231, 356
See application file for complete search history.

(56) References Cited

U.S. PATENT DOCUMENTS

| | | | | |
|---|---|---|---|---|
| 3,096,977 A | * | 7/1963 | Winkler et al. ............ 271/2 |
| 3,689,061 A | * | 9/1972 | Nystrand ............. 493/369 |
| 4,521,209 A | * | 6/1985 | DuFresne ............ 493/432 |
| 4,739,910 A | * | 4/1988 | Westphal et al. ........... 223/37 |
| 5,779,831 A | | 7/1998 | Schmitz |
| 5,788,805 A | * | 8/1998 | Herrmann ............. 156/496 |
| 6,036,805 A | * | 3/2000 | McNichols ............ 156/227 |
| 6,139,004 A | * | 10/2000 | Couillard et al. ........... 271/70 |
| 6,250,357 B1 | * | 6/2001 | Niedermeyer ........... 156/436 |
| 6,254,714 B1 | * | 7/2001 | Niedermeyer ........... 156/256 |
| 6,723,035 B2 | * | 4/2004 | Franklin et al. .......... 493/450 |
| 6,893,388 B2 | * | 5/2005 | Reising et al. .......... 493/231 |
| 2003/0226862 A1 | | 12/2003 | Vogt et al. |

FOREIGN PATENT DOCUMENTS

GB    1 314 168 A    4/1973
JP    9-131364 A    5/1997

* cited by examiner

*Primary Examiner*—Sameh H. Tawfik
(74) *Attorney, Agent, or Firm*—Birch, Stewart, Kolasch & Birch, LLP (57) ABSTRACT

A method and machine for folding and finishing training pant diapers, whereby the diapers are formed from respective flat blanks, each of which is fed to a continuously-rotating, suction-type first wheel, and is folded into a U by clamping an intermediate portion of the blank on the first wheel by means of a folding member; retaining a trailing half of the blank on the first wheel, while detaching a leading half from the first wheel by means of a continuously-rotating, suction-type second wheel; transferring the leading half to a continuously-rotating, suction-type third wheel; and gradually superimposing the leading half of the blank onto the trailing half, as the trailing half advances on the first wheel, and after first removing the folding member from the blank.

14 Claims, 6 Drawing Sheets

METHOD AND MACHINE FOR FOLDING AND FINISHING TRAINING PANT DIAPERS

The present invention relates to a method and machine for folding and finishing training pant diapers.

BACKGROUND OF THE INVENTION

In the diaper industry, diapers are normally folded by feeding a succession of flat diapers along a linear conveyor; arresting each flat diaper with a central portion positioned over a transverse opening in the linear conveyor; and folding the diaper into a U by inserting a folding member through the opening.

Though widely used, by being simple and efficient, the above method has several serious drawbacks, particularly at maximum production speed, and which derive from two factors: firstly, potential damage of the diaper, given its relatively fragile structure, by the rapid in-out movement of the folding member; and, secondly, and more importantly, the impossibility, given the way in which the folding operation is performed, of promptly controlling the position of the two halves of the diaper superimposed during the folding operation, with the result that one half of the folded diaper is offset in respect of the other.

The problem is further compounded in the relatively recent production of so-called "training pant" diapers which, after being folded into a U in the same way as conventional diapers, are joined permanently, e.g. sealed, along the lateral portions to form a closed annular girdle enabling the diaper to be used pant-fashion.

While U-folding conventional diapers does not necessarily call for a high degree of precision, the same obviously does not apply to training pants, in which case, the flat diaper must be folded extremely accurately so that the lateral portions to be joined permanently overlap perfectly.

As stated, experience has shown that the above folding method, by failing to control the folding operation and ensure precise overlapping of the two halves of the diaper, and therefore of the portions to be joined permanently, may result in an unacceptable end product, both in terms of function and appearance.

SUMMARY OF THE INVENTION

It is an object of the present invention to provide a method of folding and finishing training pant diapers, designed to ensure extremely precise folding of the diapers, and the production of diapers which are both functionally and aesthetically satisfactory.

According to the present invention, there is provided a method of folding and finishing training pant diapers, as claimed in the attached Claims.

According to the present invention, there is also provided a machine for folding and finishing training pant diapers, as claimed in the attached Claims.

BRIEF DESCRIPTION OF THE DRAWINGS

A number of non-limiting embodiments of the present invention will be described by way of example with reference to the accompanying drawings, in which.

DETAILED DESCRIPTION OF THE INVENTION

Figure 1:
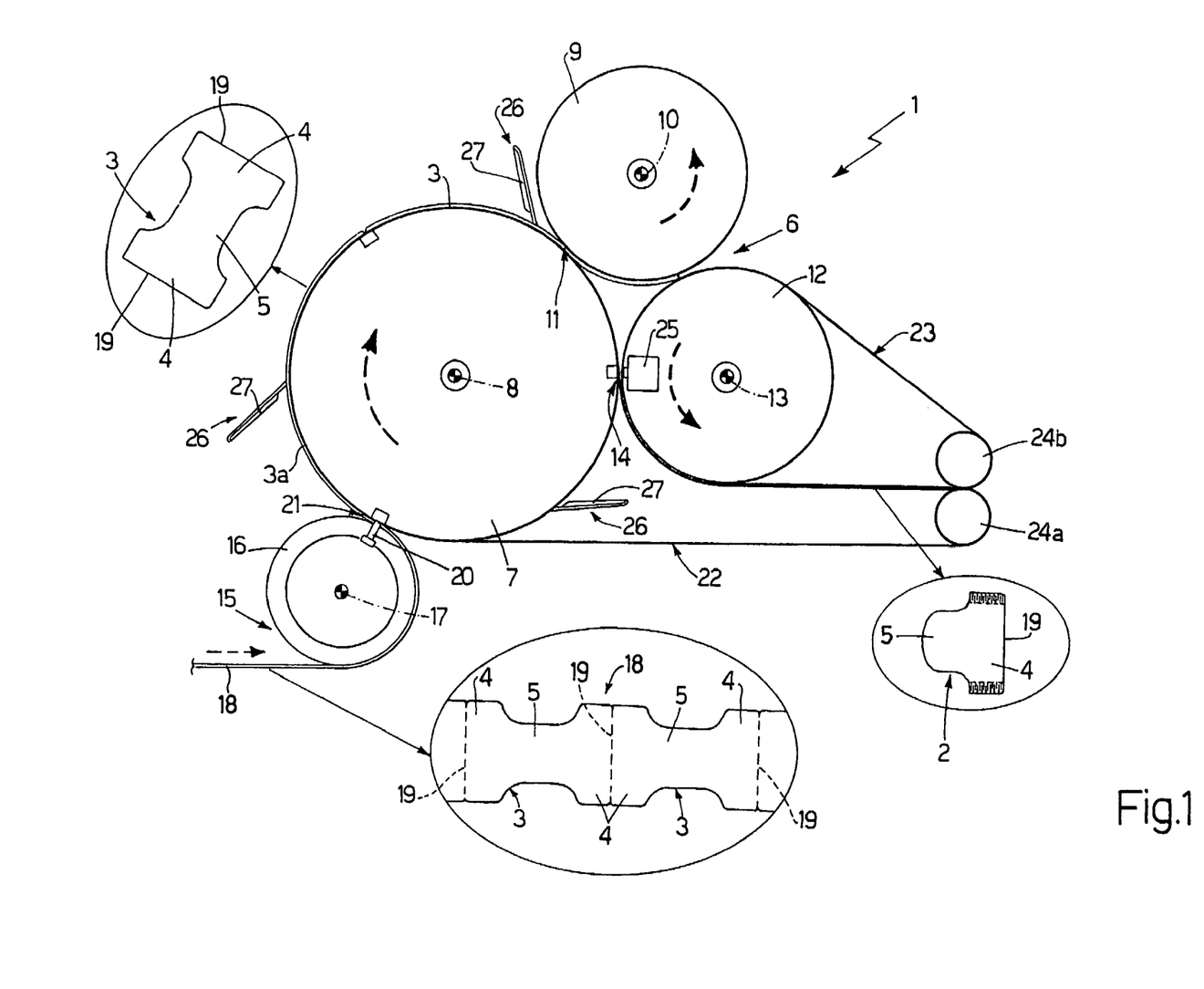
FIG. 1 shows a partial, schematic view of a first preferred embodiment of the machine according to the present invention.
Figure 2:
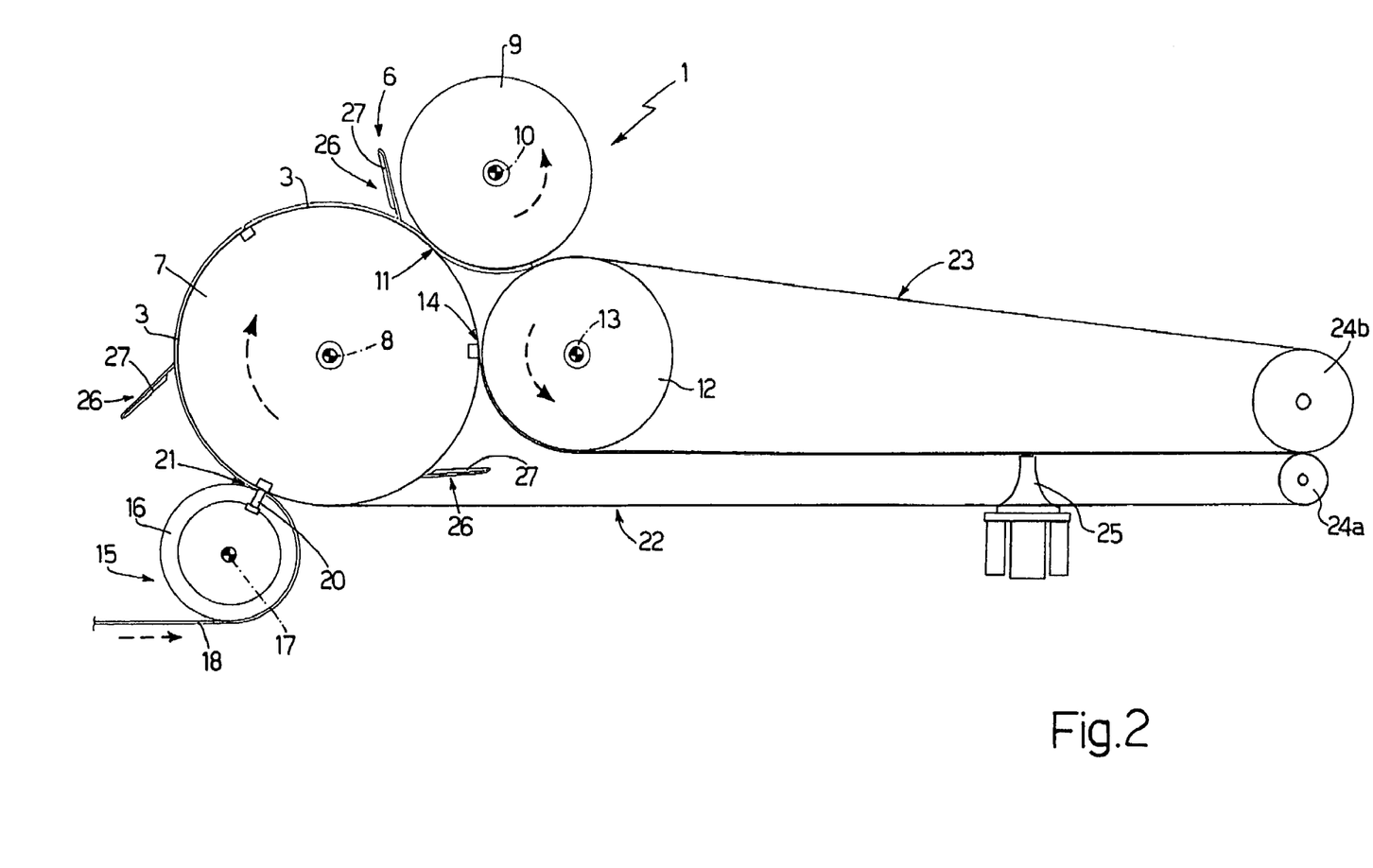
FIG. 2 shows a partial, schematic view of a second preferred embodiment of the machine according to the present invention.

Number 1 in FIGS. 1 and 2 indicates as a whole a machine for folding and finishing training pant diapers 2, i.e. diapers shaped and closed pant-fashion, by which to train babies in the use of the corresponding undergarment.

More specifically, as is known, a training pant diaper 2 comprises a closed annular girdle; and a padded crotch connected to both sides of the annular girdle to define, with the girdle, two leg holes.

As shown in the FIG. 1 details, each diaper 2 is formed from a respective flat, H-shaped blank 3 comprising two substantially rectangular transverse bands 4 which, when joined, define the annular girdle of diaper 2 as described above; and a longitudinal crosspiece 5 connecting bands 4 and defining the crotch of the finished diaper 2.

With reference to FIGS. 1 and 2, machine 1 comprises a folding unit 6, in turn comprising a main wheel 7 rotating continuously (clockwise in the drawings) about an axis 8 perpendicular to the FIG. 1 plane; a wheel 9 which rotates continuously (anticlockwise in the drawings) about an axis 10 parallel to axis 8, and is tangent to wheel 7 at a transfer station 11; and a wheel 12 which rotates continuously (anticlockwise in the drawings) about an axis 13 parallel to axes 8 and 10, is substantially tangent to wheel 9 at a point downstream from transfer station 11 in the rotation direction of wheel 9, and is tangent to wheel 7 at a folding station 14 for folding blanks 3 and located downstream from transfer station 11 in the rotation direction of wheel 7.

Wheels 7, 9 and 12 are known suction wheels, and each comprise a known perforated skirt (not shown) selectively connected to a respective known suction chamber (not shown) to retain blanks 3 on relative wheel 7, 9, 12. Blanks 3 are fed to main wheel 7 by a feed line 15, an output portion of which is defined by a wheel 16 tangent to wheel 7, at a point upstream from transfer station 11, and mounted to rotate about an axis 17 parallel to axis 8.

Along feed line 15, blanks 3 are fed longitudinally in the form of a continuous strip 18 defined by a succession of blanks 3 connected at respective bands 4. More specifically, as shown in one of the FIG. 1 details, each band 4 of a blank 3 is connected to band 4 of the contiguous blank 3 along a respective cut line corresponding, after blank 3 is detached, to a free transverse edge 19 of band 4.

For this purpose, wheel 16 is fitted with a known cutting device comprising a knife 20 which, at a cutting station 21 located at the point of tangency between wheels 7 and 16, moves to and from wheel 7 to cut strip 18 transversely into a continuous succession of individual blanks 3.

As explained in more detail below, once separated, blanks 3 are fed, starting from cutting station 21, along a folding path extending partly about wheels 7, 9 and 12, and partly coinciding with the work branches of two conveyors 22 and 23, of which, conveyor 22 is wound about wheel 7 and a return pulley 24a, and conveyor 23 is wound about wheel 12 and a return pulley 24b.

Figure 3:
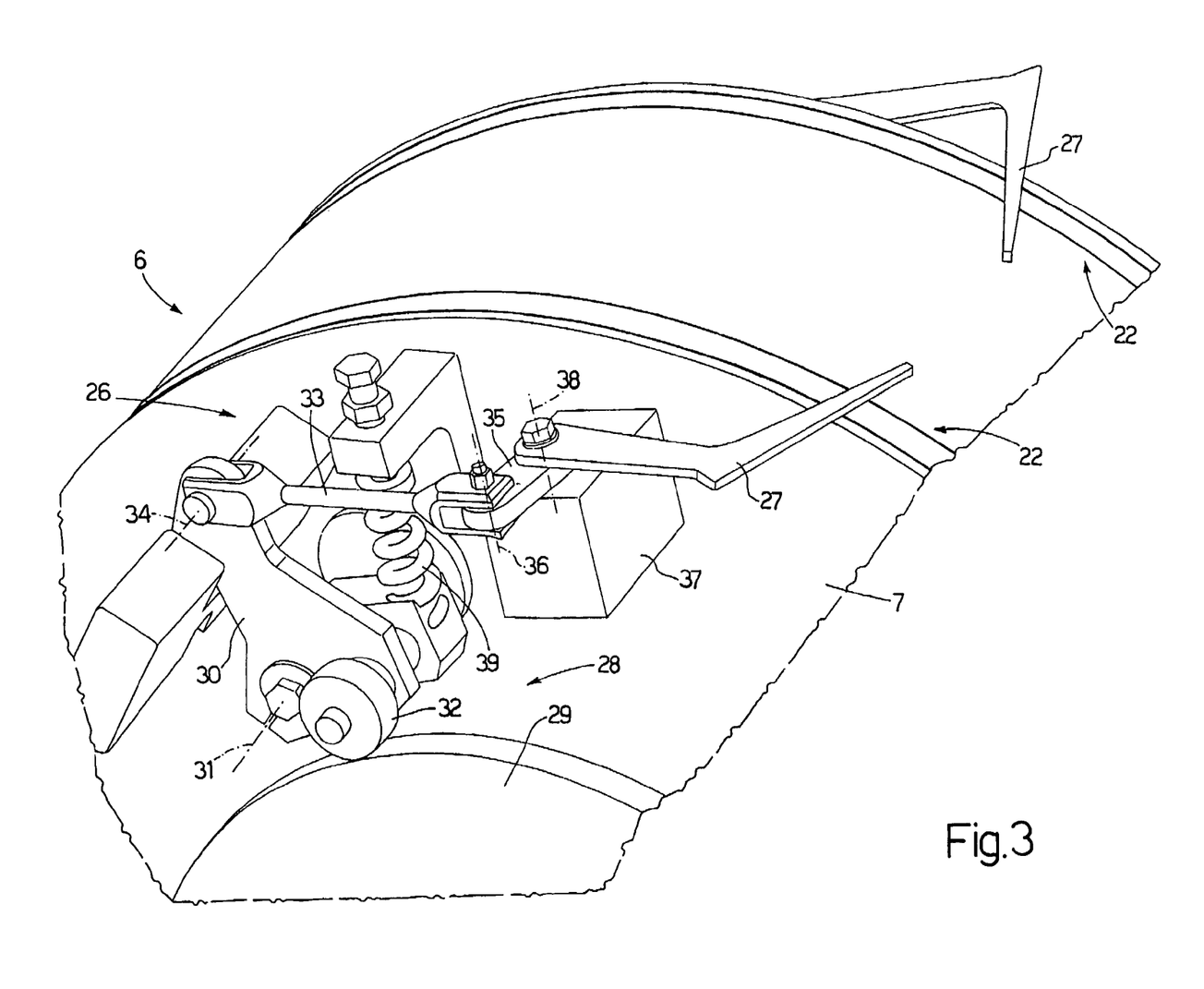
FIG. 3 shows a larger-scale view in perspective of a detail of FIGS. 1 and 2.

More specifically, as shown in FIGS. 1 and 2, pulleys 24a and 24b rotate about respective axes parallel to axis 8, are tangent to each other, and define, on relative conveyors 22 and 23, respective substantially mating work branches, which extend from folding station 14 to the point of tangency between pulleys 24a and 24b, and define a guide channel for the folded blanks 3 issuing from folding station 14. Each conveyor 22, 23 comprises (as shown in FIG. 3 relative to conveyor 22) two parallel belts, each located close to a respective free edge of relative wheel 7, 12 and of relative pulley 24a, 24b.

As shown in FIG. 1, machine 1 also comprises a heat-sealing device 25 located at folding station 14, and which, as explained below, provides for heat sealing the end portions of bands 4, as each folded blank 3 travels through folding station 14, to form the closed annular girdle of relative diaper 2.

In the FIG. 2 variation, sealing device 25 is an ultrasound sealing device which, as opposed to being located between wheels 7 and 12, is located at a point downstream from folding station 14, along the guide channel defined by the work branches of conveyors 22 and 23. Also, as compared with the previous embodiment, pulleys 24a and 24b are located further away from wheels 7 and 12, so that the respective work branches defining the guide channel of blanks 3 are longer.

In other embodiments, not shown, ultrasound sealing device 25 may be located at folding station 14, and heat-sealing device 25 may be located downstream from folding station 14, along the guide channel defined by conveyors 22 and 23.

In a further variation, sealing device 25 may be replaced by a different type of connecting device for connecting bands 4 permanently or releasably, such as a glue or Velcro applicator.

As shown in FIGS. 1 and 2, and in more detail in FIG. 3, wheel 7 is equipped with a number of pairs of folding devices 26 fitted to wheel 7, equally spaced about axis 8, and each comprising two identical folding devices 26 located symmetrically on opposite sides of wheel 7, close to the cylindrical peripheral surface of wheel 7.

As shown in FIG. 3, each folding device 26 comprises a clamp 27 operated by an actuating device 28 to move—in time with clamp 27 of the corresponding folding device 26 and to and from the cylindrical outer surface of wheel 7—between a raised rest position, and a lowered work position in which clamp 27 is pressed against the outer cylindrical surface of wheel 7 to clamp an intermediate portion of a relative blank 3 on wheel 7, as explained in more detail below.

Actuating device 28 comprises a cam 29 fitted to the drive shaft of wheel 7; and a transmission which is interposed between cam 29 and clamp 27 to move clamp 27 to and from the raised rest position in response to continuous rotation of cam 29, and in turn comprises a rocker arm 30 hinged to wheel 7 to oscillate about an axis 31 parallel to axis 8, and having a first arm which extends from axis 31 towards cam 29 and is fitted on its free end with a roller cam follower 32 rolling on cam 29.

Rocker arm 30 also comprises a second arm which extends substantially crosswise to the first arm and constitutes a crank of an oblique articulated quadrilateral comprising a connecting rod 33, hinged to the free end of the second arm to oscillate about an axis 34 parallel to axis 31, and a second crank defined by an arm 35, which extends substantially crosswise to connecting rod 33 and the second arm, and is hinged to the free end of connecting rod 33 to oscillate about an axis 36 crosswise to axis 34 and sloping with respect to a radial plane through axis 8 of wheel 7.

At the opposite end, arm 35 is hinged to a block 37, integral with wheel 7, to oscillate about an axis 38 parallel to axis 36, and is fitted rigidly with clamp 27.

Oscillation of rocker arm 30 about axis 31 is therefore converted, by connecting rod 33, to oscillation of arm 35 about axis 38, thus moving clamp 27 from the raised rest position to the lowered work position, or vice versa.

Actuating device 28 also comprises a push spring 39 compressed between rocker arm 30 and a bracket integral with wheel 7, to keep cam follower 32 in contact with cam 29 in use.

Operation of machine 1 will now be described as of FIG. 1, and with particular reference to one blank 3 which, for the sake of clarity, is indicated hereinafter as blank 3a.

In the FIG. 1 operating configuration, blank 3a, just cut off strip 18 by knife 20, is located immediately downstream from cutting station 21, is retained on wheel 7 by suction, and is positioned with its inner surface (i.e. the surface directly contacting the skin when relative diaper 2 is in use) facing outwards of wheel 7.

It should be pointed out that wheel 7 and wheel 16 are so synchronized, and the number of folding devices 26 along the periphery of wheel 7 is such that, as a blank 3 is fed to wheel 7, a pair of clamps 27 is always located at a mid-portion of blank 3.

As of the FIG. 1 position, blank 3a is fed by wheel 7 along the folding path until the leading edge 19 of blank 3a reaches transfer station 11.

At this point, suction in the sector of wheel 7 immediately downstream from transfer station 11 is at least partly cut off, and suction in the sector of wheel 9 immediately downstream from transfer station 11, in the rotation direction of wheel 9, is activated.

As a result, the leading edge 19 of blank 3a is sucked onto wheel 9, and, as wheels 7 and 9 rotate continuously, the leading half of blank 3a is detached from wheel 7 and gradually winds onto the cylindrical outer surface of wheel 9.

Figure 4:
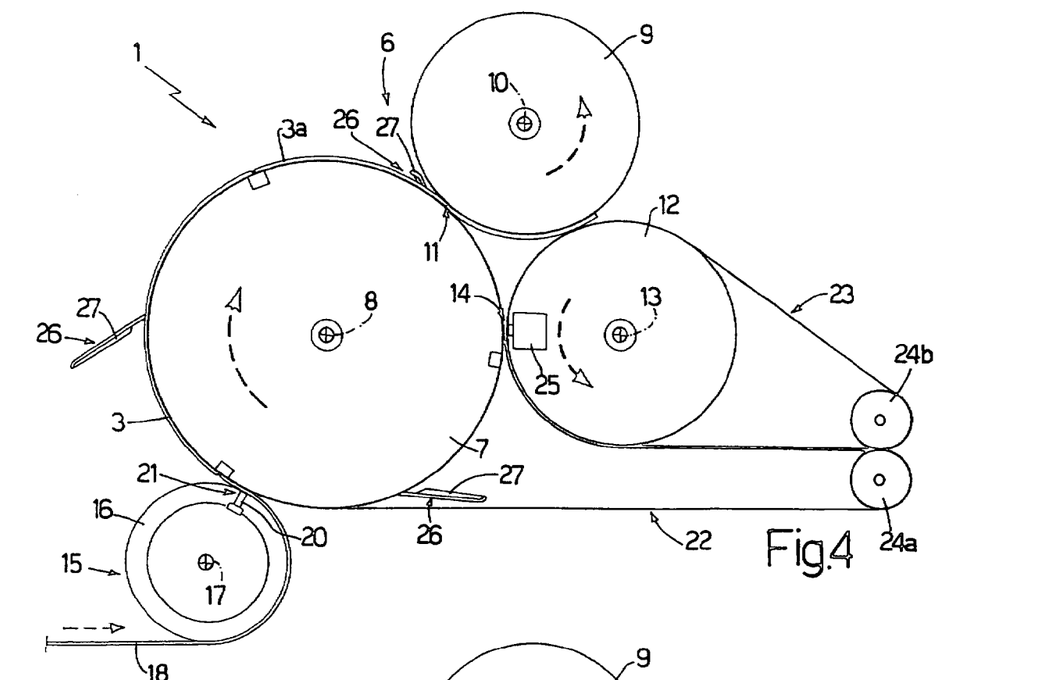
FIGS. 4-9 show the FIG. 1 machine in respective different operating configurations.

As shown in FIG. 4, before the leading half of blank 3a is laid completely on wheel 9, the two clamps 27 located at the mid-portion of blank 3a are moved by respective actuating devices 28 from the raised rest position to the lowered work position to clamp the mid-portion of blank 3a on wheel 7.

When the leading half of blank 3a is wound completely on wheel 9, and clamps 27, in the lowered work position, have travelled through transfer station 11 (FIG. 5), suction in the sector of wheel 7 immediately downstream from transfer station 11 is restored, so that the trailing half of blank 3a passing transfer station 11 remains firmly attached to wheel 7.

Figure 5:
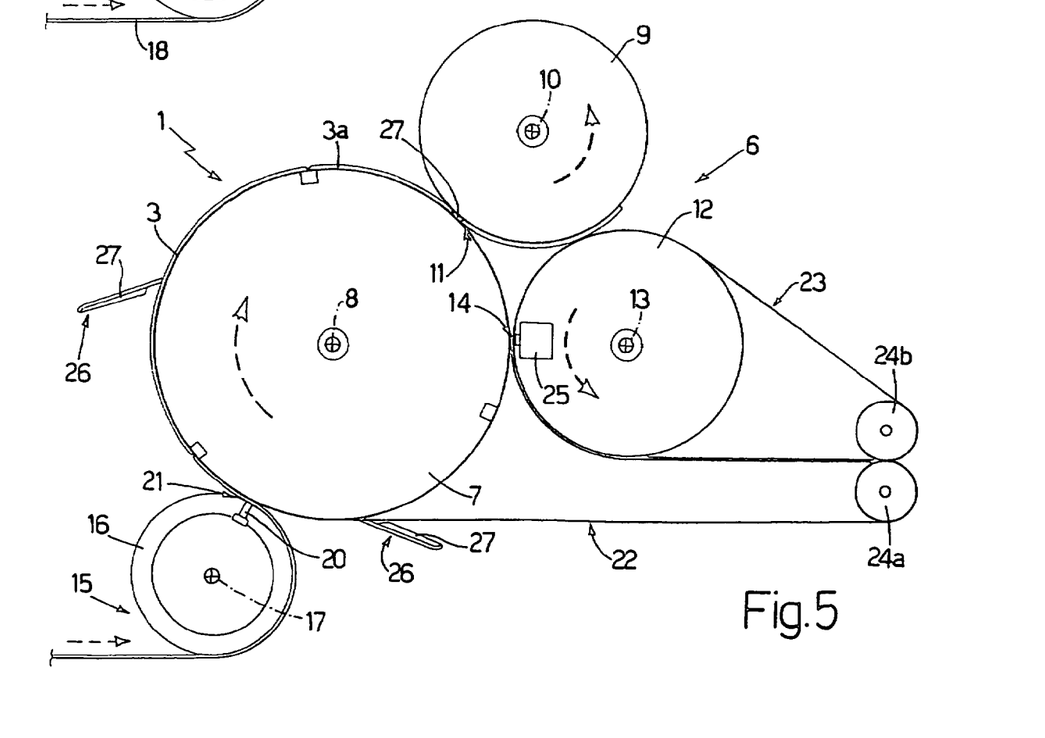

At the same time, suction in the sector of wheel 9 between transfer station 11 and the point of tangency between wheel 9 and wheel 12 is cut off, so that, as the trailing half of blank 3a moves away from transfer station 11, the leading half is detached easily from the surface of wheel 9.

That is, since clamps 27 secure blank 3a firmly to wheel 7, and the leading half must necessarily follow the trailing half, the trailing half would tear the leading half off wheel 9, thus damaging blank 3a, if the leading half were not sufficiently free to come away from wheel 9.

Figure 6:
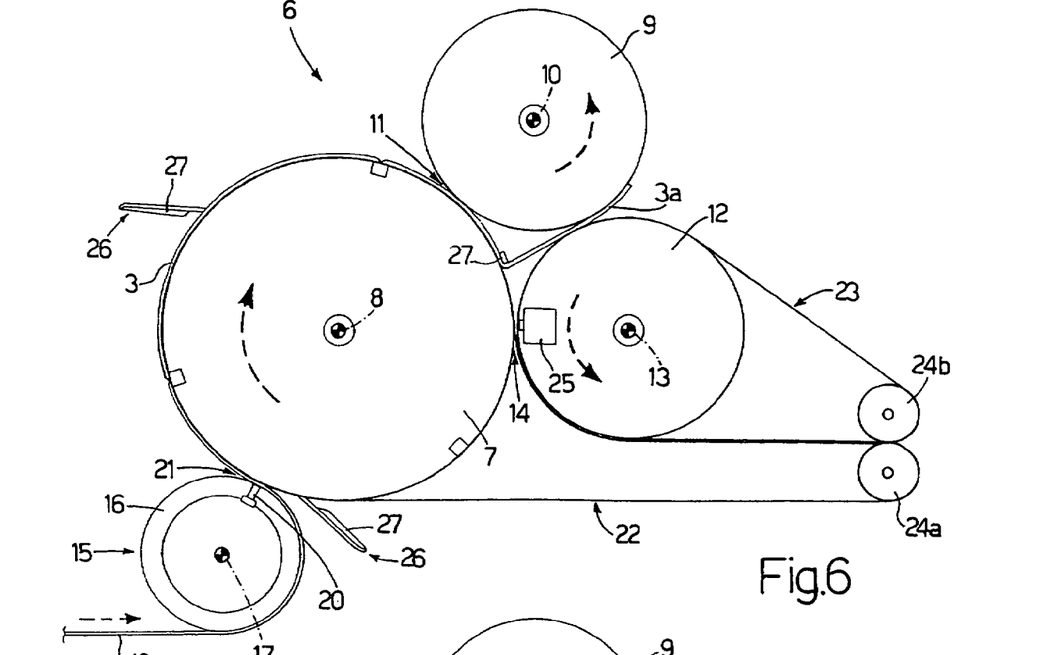

However, to ensure the leading half is detached gradually from wheel 9, as opposed to coming away completely from wheel 9 and "collapsing" onto the trailing half, suction is maintained in the portion of wheel 9 corresponding to the portion of the leading half close to edge 19 (FIG. 6), and is activated in the sector of wheel 12 extending between the point of tangency with wheel 9 and folding station 14, so that the leading half of blank 3a, as it is detached from wheel 9, adheres to wheel 12 and remains flat.

Figure 7:
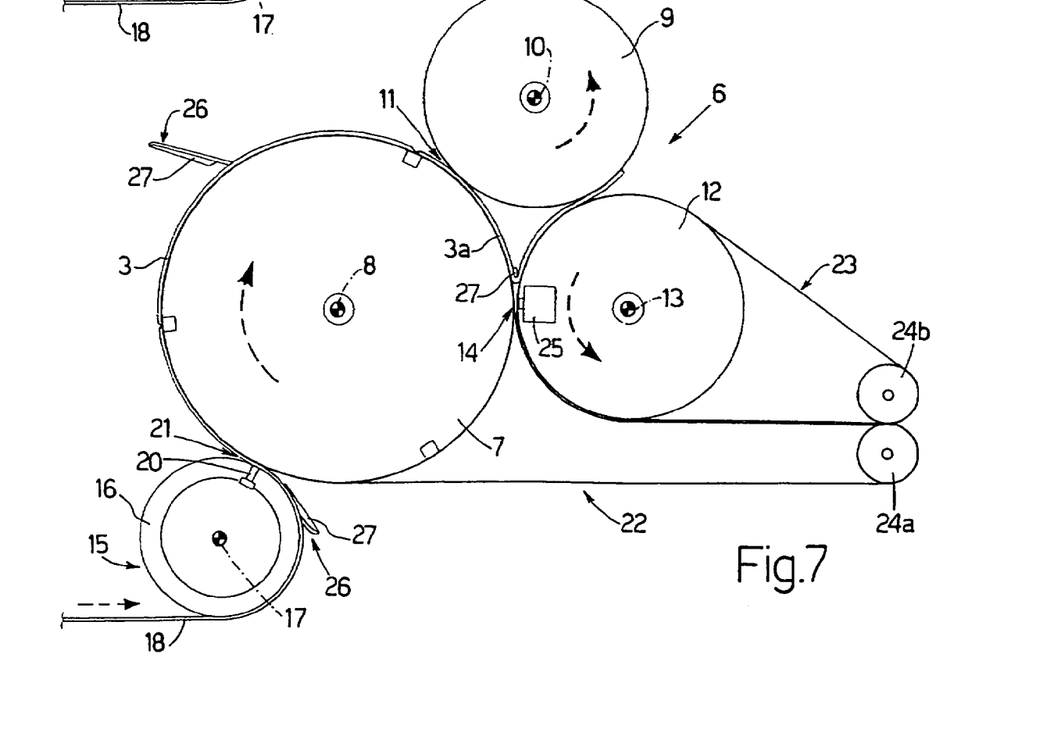

As shown in FIG. 7, continuous rotation of wheels 7 and 12 gradually brings the leading and trailing halves together to fold blank 3a into a U. And, on reaching a point immediately upstream from folding station 14, clamps 27 are moved by actuating device 28 from the lowered work position to the raised rest position.

Figure 8:
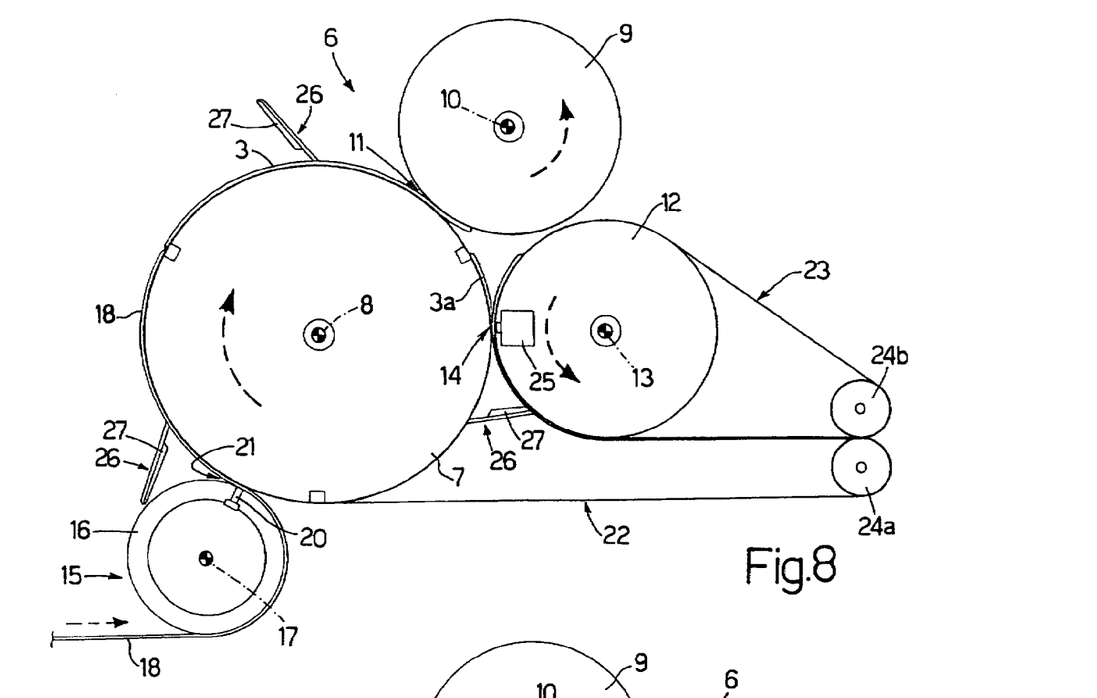
Figure 9:
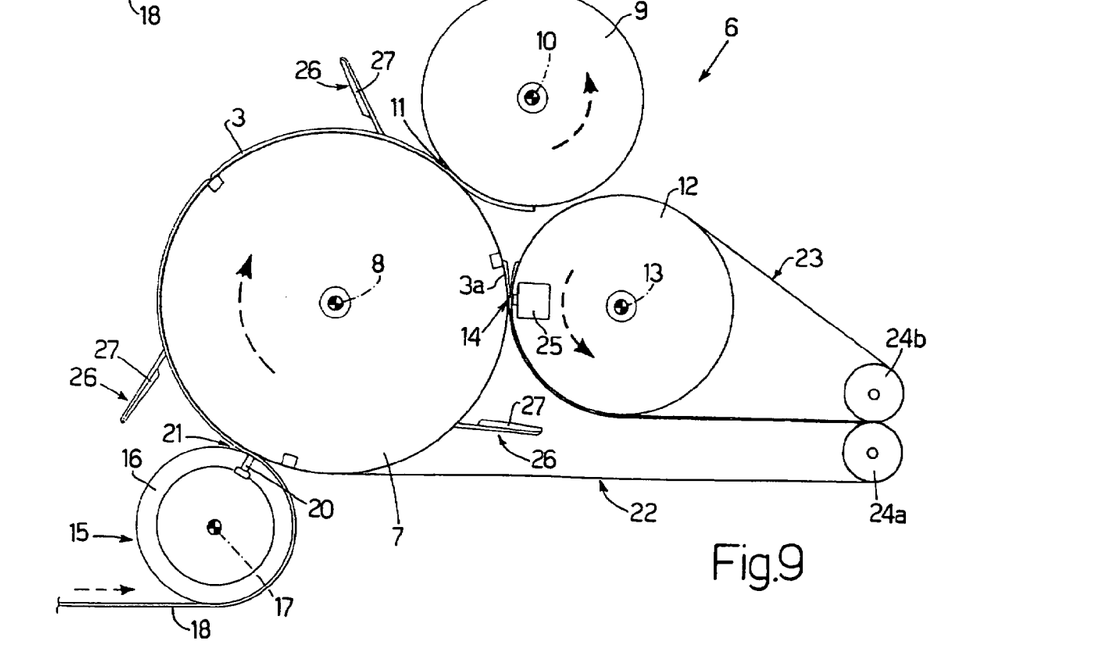

From this point on, as blank 3a is fed gradually through folding station 14 and then inserted, downstream from folding station 14, between the belts of conveyors 22 and 23 (FIGS. 8 and 9), the leading half and trailing half of blank 3a are superimposed completely.

With reference to the FIG. 1 embodiment, diaper 2 is finished, i.e. the end portions of bands 4 are sealed to form the closed annular girdle, as bands 4 travel through folding station 14 and past sealing device 25.

In other words, on machine 1, each flat blank 3 is fed to folding station 14 by a first conveyor—in this case, wheel 7; the trailing half of each blank 3 is clamped on the first conveyor upstream from folding station 14 in the travelling direction of the first conveyor; the leading half of each blank 3 is transferred from the first conveyor to a further conveyor—in this case, wheel 12—which cooperates with the first conveyor to fold blanks 3 into a U at folding station 14; and transverse bands 4 of each U-folded blank 3 are joined to form the relative closed annular girdle.

The leading half of each blank 3 is transferred from wheel 7 to wheel 12 via wheel 9. However, in a variation not shown, wheel 9 may be replaced by a continuous or intermittent mechanism with or without suction.

Once completed, diaper 2, gripped between the belts of conveyors 22 and 23, is carried off folding unit 6 and fed to a known packing unit (not shown).

In the FIG. 2 variation, on the other hand, the folded but as yet unsealed blank 3 is carried away from folding station 14, between the belts of conveyors 22 and 23, and is completed later by sealing device 25.

In this connection, it should be pointed out that the two belts of each conveyor 22, 23 are wound about relative wheel 7, 12 and about relative pulley 24a, 24b at such a distance apart that, when diaper 2 is inserted between the belts downstream from folding station 14, the belts engage the end portions of bands 4 to keep the two halves of blank 3 perfectly superimposed, and, in particular, to prevent the end portions of bands 4 from shifting with respect to each other before being sealed.

Also for this purpose, suction is preferably activated in a sector of wheel 12 located immediately downstream from folding station 14, to retain the blank 3 issuing from folding station 14 firmly in contact with wheel 12.

To conclude, it should be pointed out that the system for selectively activating and cutting off suction on wheels 7, 9 and 12 provides, at the successive transfer and folding stages, for accurate handling of blank 3, with no sharp changes in direction, and, in particular, for continually controlling the position of blank 3 with respect to wheels 7, 9 and 12 to ensure, at the folding stage, precise overlapping of the two halves of blank 3 and perfect alignment of bands 4 to be sealed to form the closed annular girdle of diaper 2.

The invention claimed is:

1. A method of folding and finishing training pant diapers, wherein each diaper includes a closed annular girdle, and a crotch connected to the girdle to define two leg openings, and wherein each diaper is formed from a respective H-shaped flat blank comprising two transverse bands, and a longitudinal crosspiece connecting the bands and defining said crotch of the diaper; said method comprising the steps of conveying the flat blank on a first conveyor;

clamping an intermediate portion of the blank on the first conveyor and, at the same time, gradually detaching a leading half of the blank, in the travelling direction of the blank, from the first conveyor by a second conveyor, while retaining a trailing half of the blank on the first conveyor;

transferring the leading half from said second conveyor to a third conveyor as the trailing half is advanced on the first conveyor;

folding the blank into a U-shaped configuration by rotating the third conveyor to gradually superimpose the leading half and the trailing half together, and folding the blank by conveying it though a folding station interposed between the first and third conveyor; and joining the transverse bands of the blank to form the closed annular girdle.

2. The method as claimed in claim 1, wherein said first, second, and third conveyor are continuously-operated.

3. The method as claimed in claim 1, wherein the first, second, and third conveyors are suction conveyors.

4. The method as claimed in claim 3, wherein, during all the aforementioned steps preceding the step of joining the bands, the trailing half of the blank is retained at all times on the first conveyor by suction.

5. The method as claimed in claim 4, wherein the leading half of the blank is detached from the first conveyor by gradually transferring the leading half onto the second conveyor and retaining the leading half on the second conveyor by suction.

6. The method as claimed in claim 5, wherein said first, said second, and said third conveyor are circular conveyors rotating about respective parallel axes; the first conveyor and the second conveyor being counter-rotating and tangent at a transfer station, and the first and third conveyor being counter-rotating and tangent at said folding station wherein the step of detaching the leading half from the first conveyor is performed by at least partly cutting off suction on the first conveyor downstream from the transfer station in the travelling direction of the first conveyor, and by activating suction on the second conveyor downstream from the transfer station in the travelling direction of the second conveyor.

7. The method as claimed in claim 6, wherein the step of transferring the leading half of the blank from the second conveyor to the third conveyor comprises the substeps of at least partly cutting off suction on the second conveyor, and at the same time activating suction on the third conveyor.

8. The method as claimed in claim 6, wherein the step of clamping an intermediate portion of the blank on the first conveyor is performed by means of a respective folding device fitted to the first conveyor and associated with the blank; the folding device comprising at least one folding member movable from a raised rest position to a lowered work position and wherein the folding member is pressed against the first conveyor.

9. The method as claimed in claim 8, wherein the folding member is restored from the lowered work position to the raised rest position before the blank begins travelling through the folding station.

10. The method as claimed in claim 8, wherein each folding device comprises two identical folding members located on the first conveyor, on opposite sides of the blank.

11. The method as claimed in claim 1, wherein the bands are joined at the folding station.

12. The method as claimed in claim 1, wherein the bands are joined downstream from the folding station.

13. The method as claimed in claim 1, further comprising the step of removing each folded blank issuing from the folding station, by means of removing means designed to maintain the two halves of the folded blank firmly superimposed.

14. The method as claimed in claim 13, wherein said removing means comprises two belt conveyors having respective work branches substantially mating with each other and defining there-between a guide channel for the folded blanks.

* * * * *